(12) United States Patent
Ryu et al.

(10) Patent No.: US 9,610,378 B2
(45) Date of Patent: Apr. 4, 2017

(54) ANTIMICROBIAL WOUND-COVERING MATERIAL AND METHOD FOR MANUFACTURING SAME

(71) Applicant: CG BIO CO., LTD., Gyeonggi-do (KR)

(72) Inventors: Hyun Seung Ryu, Gyeonggi-do (KR); Jun Kyu Park, Gyeonggi-do (KR); Jun Hyuk Seo, Gyeonggi-do (KR); Young Koo Lee, Gyeonggi-do (KR)

(73) Assignee: CG Bio Co., Ltd., Gyeonggi-do (KR)

( * ) Notice: Subject to any disclaimer, the term of this patent is extended or adjusted under 35 U.S.C. 154(b) by 0 days.

(21) Appl. No.: 14/372,225

(22) PCT Filed: Dec. 28, 2012

(86) PCT No.: PCT/KR2012/011759
§ 371 (c)(1),
(2) Date: Jul. 15, 2014

(87) PCT Pub. No.: WO2013/109004
PCT Pub. Date: Jul. 25, 2013

(65) Prior Publication Data
US 2014/0377331 A1  Dec. 25, 2014

(30) Foreign Application Priority Data

Jan. 19, 2012 (KR) .................. 10-2012-0006274

(51) Int. Cl.
*A61L 15/28* (2006.01)
*A61L 15/18* (2006.01)
*A61L 15/44* (2006.01)
*A61L 15/46* (2006.01)

(52) U.S. Cl.
CPC .............. *A61L 15/28* (2013.01); *A61L 15/18* (2013.01); *A61L 15/44* (2013.01); *A61L 15/46* (2013.01); *A61L 2202/26* (2013.01); *A61L 2300/104* (2013.01); *A61L 2300/404* (2013.01); *A61L 2300/606* (2013.01); *A61L 2300/802* (2013.01); *A61L 2400/12* (2013.01)

(58) Field of Classification Search
None
See application file for complete search history.

(56) References Cited

U.S. PATENT DOCUMENTS

| | | | |
|---|---|---|---|
| 3,624,201 A | 11/1971 | Balassa | |
| 3,632,754 A | 1/1972 | Balassa | |
| 3,914,413 A | 10/1975 | Balassa | |
| 4,651,725 A | 3/1987 | Kifune et al. | |
| 4,699,135 A | 10/1987 | Motosugi et al. | |
| 5,635,201 A * | 6/1997 | Fabo | A61F 13/0276 424/443 |
| 6,087,549 A | 7/2000 | Flick | |
| 6,719,987 B2 | 4/2004 | Langford et al. | |
| 6,897,349 B2 | 5/2005 | Gibbins et al. | |
| 2005/0154361 A1* | 7/2005 | Sabesan | A01N 43/16 604/365 |
| 2008/0146983 A1* | 6/2008 | Park | A61F 13/00008 602/46 |
| 2010/0113871 A1 | 5/2010 | Dias et al. | |
| 2010/0203144 A1* | 8/2010 | Laurencin | A61L 27/04 424/489 |
| 2011/0070423 A1* | 3/2011 | Jayakody | A61L 15/26 428/309.9 |

FOREIGN PATENT DOCUMENTS

| | | |
|---|---|---|
| JP | 57-143508 | 9/1982 |
| JP | 05-092925 | 4/1993 |
| KR | 1020000014189 A | 3/2000 |
| KR | 100296738 B1 | 5/2001 |
| KR | 1020010067991 A | 7/2001 |
| KR | 1020010079260 A | 8/2001 |
| WO | WO2005/077329 A1 | 8/2005 |

* cited by examiner

*Primary Examiner* — Jessica Worsham
(74) *Attorney, Agent, or Firm* — Rosenberg, Klein & Lee

(57) ABSTRACT

The present invention relates to an antimicrobial wound dressing comprising chitosan-silver nanoparticles and a preparation method thereof The antimicrobial wound dressing is prepared by coating a wound dressing with chitosan and silver and drying the coated wound dressing and has an excellent property of releasing silver nanoparticles in a sustained manner.

6 Claims, 3 Drawing Sheets

< CONTROL >

< EXAMPLE 6 >

< CONTROL >

< EXAMPLE 6 >

ANTIMICROBIAL WOUND-COVERING MATERIAL AND METHOD FOR MANUFACTURING SAME

TECHNICAL FIELD

The present invention relates to an antibacterial wound dressing and a preparation method thereof, and more particularly to an antibacterial wound dressing, which has an excellent property of releasing an antimicrobial material, and thus can maintain antibacterial activity in the wound area of the patient's skin for a long period of time, and a preparation method thereof.

BACKGROUND ART

The skin is an organ that covers the entire skin of the body and performs immune functions. Also, it is a tissue that protects the body from various harmful environments such as external microorganisms, UV rays and chemical substances and inhibits the evaporation of water from the body to prevent the dehydration of the body and control the body temperature. The skin should be strong against physical stimuli, should be elastic and should perform its functions when the human body maintains life. Thus, when the skin is wounded, such important functions become abnormal so that the human body is out of balance.

Wound treatment is a biological process for restoring tissue broken by any trauma or surgery and is an important process enabling the patient to be treated. Methods for treating wounds can be largely divided into a method of treating a wound by maintaining it in a dry state using, for example, a gauze dressing, and a method of maintaining a wound in a moist state.

The results of clinical studies, which have been conducted on moist dressings that maintain wounds in a moist environment, demonstrate the safety and effectiveness of a moist environment provided by a moist dressing in the treatment of acute wounds and chronic wounds that have been considered to be impossible to treat. In other words, in a moist environment, wound healing proceeds efficiently, because regenerated epithelial cells are easily developed along the wound surface and because substances, such as polymorphonuclear leukocytes, macrophages, proteases and cell growth factors, which are contained in exudate and involved in wound healing, can easily perform their functions in the moist environment.

Meanwhile, silver (Ag) has been known to have excellent antibacterial and bactericidal activities compared to other metals, and the antibacterial action and mechanism of silver has been scientifically verified through systematic studies conducted by many scientists together with the development of modem science. Silver has been used long ago as a perfect antibacterial material in the medical field, and the effect thereof was considered to be equal to artificial antibiotics prepared by synthesis, and silver causes no side effects.

At present, commercial antibacterial dressings comprising silver exist. The use of silver in cotton and bandages in hospitals is because the effects of silver against burns, infections, inflammation and other microbial infections were already scientifically proven. Colloidal silver as an aqueous solution is a natural antibiotic approved by the FDA and is currently used as an effective drug together with melatonin and DHEA in the USA. However, prior art technologies of absorbing silver into cloth using electrolyzed water and drying the cloth in order to use silver as medical supplies have shortcomings in that the content of silver is insignificant and silver is detached from the medical supplies during preparation, transport and use, and thus the effect of silver is rapidly lost.

U.S. Pat. Nos. 6,719,987 and 6,087,549 disclose electro-coating silver nanoparticles on a polyurethane mesh fiber having a monolayer structure, but have shortcomings in that silver is excessively contained, and thus is highly toxic against normal cells, and in that silver is detached from the product. In addition, there is also a shortcoming in that the product lacks the capability to absorb exudate, and thus cannot provide a moist environment. In addition, U.S. Pat. No. 6,897,349 discloses physically diffusing or dispersing silver nanoparticles, which have been precipitated by a chemical reaction, between fiber tissues, but the product disclosed therein does not exhibit sufficient antibacterial activity and sufficient therapeutic effects due to its low silver content. In addition, products obtained using such silver nanotechnologies have common problems in that the size and shape of nanoparticles are not uniform, it is not easy to control the particle size distribution, it is difficult to control the concentration and content of silver, and the production cost is high.

Meanwhile, chitosan is a kind of polysaccharide present in nature and is a compound obtained by deacetylating chitin contained in the shell of crabs and shrimps, the bone of cuttlefishes, and the cell wall of microorganisms such as fungi and bacteria. It has been used in various industrial fields from the middle of 1980s. The major application of such chitosan was limited to wastewater treatment applications, including flocculants, heavy metal adsorbents, and dye wastewater purifying agents, and agricultural applications, including soil improvers, insecticides, plant antiviral agents, and agricultural chemicals. However, as the advantages and various characteristics of chitosan have been found, the range of application of chitosan has been expanded to the food and beverage field, the health and hygiene field, the cosmetic field, the fiber-related field, and the medical field. Particularly, chitosan have received attention as a material usable as a medical material from 1990s, the use of chitosan in wound healing agents, artificial skins, medicinal materials, blood coagulants, artificial kidney membranes, biodegradable surgical sutures, and antimicrobial materials, has been reported.

More specifically, German Patent Nos. 1,906,155 and 1,906,159, which can be considered the first patents relating to wound dressings related to chitin and chitosan, disclose that chitin powder shows an excellent effect on wound repair, and U.S. Pat. Nos. 3,632,754 and 3,914,413 disclose that chitin promotes wound healing and is dissolved in lysozymes, indicating that it can be dissolved in a physiological environment. In addition, Japanese Patent Laid-Open Publication No. Sho 57-143508 discloses a gauze prepared from chitin fiber, and Japanese Patent Laid-Open Publication No. Hei 5-92925 describes the facts that the use of chitosan/cotton and chitin/cotton as a burn treating agent shows excellent effects of protecting wounds and alleviating pain, and it discloses a process of preparing chitin sponge by dispersing liquid chitin in water at a concentration of 1.5% (w/v), and pouring the dispersion onto a polystyrene film, followed by freeze drying.

Moreover, U.S. Pat. No. 4,651,725 discloses a method of preparing a wound dressing made of a non-woven fabric of chitin fiber; U.S. Pat. No. 4,699,135 discloses a method of preparing a wound dressing made of a non-woven fabric or fibrous sheet of a fibrous chitin body; Korean Patent Laid-Open Publication No. 2001-79260 discloses a method of preparing a dressing material using cultured chitosan short fiber; Korean Patent Laid-Open Publication No. 2001-67991 discloses a to method of preparing a functional fiber containing chitosan; and Korean Patent Laid-Open Publication No. 2000-14189 discloses a method of preparing a nonwoven fabric for wound treatment using Chitin, chitosan and alginic acid.

Conventional gauze-type dressings as described above easily absorb a wound exudate, but have problems in that they have no ability to defend against external bacterial infections, maintain a wound in a dry state to delay wound treatment, and stick to the wound surface so that they are not easily replaced and cause damage to newly formed tissue and pain. In addition, there is an inconvenience in that the dressing should be replaced several times a day in the initial stage of wound healing, because a large amount of exudate occurs in the initial stage.

Wound-healing dressings prepared from chitin and chitosan that are natural polymers have advantages over conventional products prepared from synthetic polymers. Wound-healing dressing products comprising chitin/chitosan have high biocompatibility compared to conventional products, and thus exhibit an excellent effect of treating wounds themselves. In addition, these products have high abilities to adsorb harmful chemical substances and heavy metals, and thus can exhibit the effect of neutralizing a poison.

The present inventors have paid attention to the above-described problems occurring in the prior art and the effects of the natural polymer chitosan and conducted many studies on an antibacterial wound dressing which has sufficient antibacterial activity and an excellent ability to absorb exudate so as to provide a moist environment, and also has an excellent property of releasing an antibacterial substance in a sustained manner, and thus can maintain antibacterial activity in the wound area of the patient's skin for a long period of time. As a result, the present inventors have found that, when silver is mixed with chitosan, chitosan is ionically bonded to silver to form fine chitosan-silver nanoparticles which are uniformly coated on a wound dressing, which then has an excellent property of releasing the antibacterial material silver in a sustained manner, thereby completing the present invention.

DISCLOSURE

Technical Problem

Therefore, it is an object of the present invention to provide an antibacterial wound dressing, which has sufficient antibacterial activity against various pathogenic bacteria while having minimal toxicity against normal cells, does not stick to the wound surface while absorbing exudate to provide a moist environment, and can release chitosan-silver nanoparticles in a sustained manner so as to maintain antibacterial activity for a long period of time, and a preparation method thereof.

Other objects of the present invention will be clearly understood by those skilled in the art from the following detailed description of the invention.

Technical Solution

In order to accomplish the above object, the present invention provides a method for preparing an antibacterial wound dressing, the method comprising the steps of: preparing an antibacterial coating solution using water-soluble chitosan and a silver compound; adsorbing and coating the prepared coating solution onto a foam dressing; and drying the foam dressing adsorbed with coating solution, thereby obtaining a wound dressing having chitosan-silver nanoparticles dispersed therein.

The method for preparing the wound dressing according to the present invention may further comprise, after coating the foam dressing, a step of blowing air into the foam dressing to ensure pores.

The method for preparing the wound dressing according to the present invention may further comprise, alter drying the foam dressing, a step of crosslinking the chitosan-silver nanoparticles. Herein, the crosslinking is performed by spraying a chitosan crosslinking solution containing $CaCl_2$, glutaraldehyde or tripolyphosphate (TPP) onto the foam dressing.

The antibacterial coating solution in the present invention may have a chitosan concentration of 0.075-10% w/v and a silver compound concentration of 0.01-10% w/v, preferably 0.1-6% w/v.

The coating solution may be coated onto the foam dressing by spray coating, dip coating, flow coating or spin coating.

The present invention also provides an antibacterial wound dressing having chitosan-silver nanoparticles dispersed therein.

Advantageous Effects

According to the present invention, there is provided an antibacterial wound dressing having an excellent sustained-release property, from which chitosan-silver nanoparticles can be released slowly so that their antibacterial activity can be maintained in the wound area of the skin in a moist environment for a long period of time.

MODE FOR INVENTION

Hereinafter, the present invention will be described in further detail with reference to the accompanying drawings.

Figure 1:
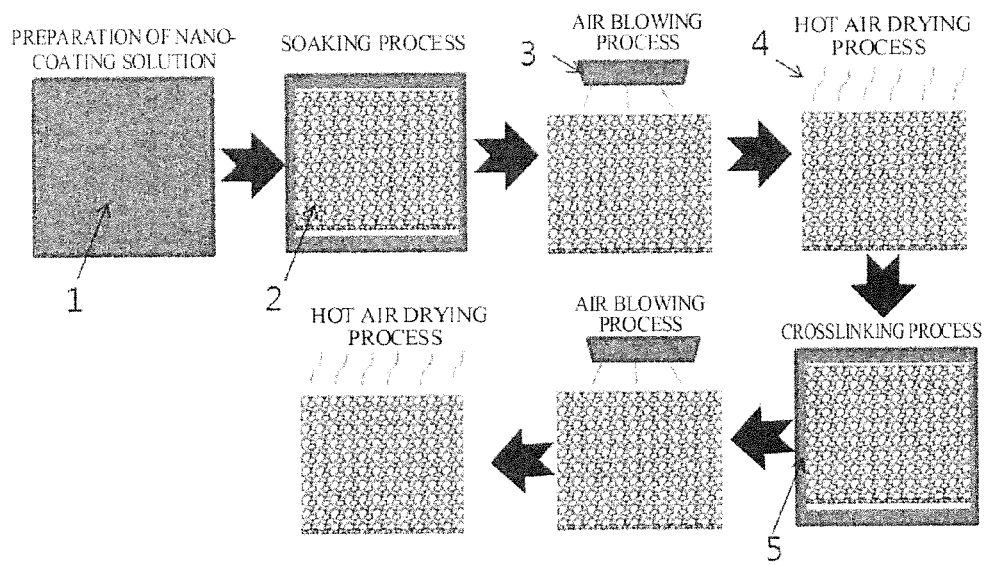
FIG. 1 is a flowchart showing a process for preparing an antibacterial wound dressing according to the present invention.

As shown in FIG. 1, in order to prepare a wound dressing according to the present invention, an antibacterial coating solution is prepared using water-soluble chitosan and a silver compound.

The water-soluble chitosan preferably has a molecular weight of 500-200,000 Da in view of efficient coating and water solubility. Examples of the water-soluble chitosan include water-soluble chitosan lactate, water-soluble chitosan chloride, water-soluble chitosan ascorbate, and water-soluble chitosan derivatives such as water-soluble lowmolecular-weight chitosan. Examples of water-soluble chitosan derivatives include chitosan-PEG, chitosan-bile acid, etc.

The concentration of chitosan in the coating solution is preferably 0.075-10% w/v. If the concentration of chitosan is too low, the wound dressing will not exhibit sufficient antibacterial activity, and if the concentration of chitosan is too high, a non-uniform coating layer can be undesirably formed.

Meanwhile, examples of a silver-containing compound that may be used in the present invention include silver halide compounds such as silver bromide, silver iodide, silver fluoride or silver chloride, silver nitrate ($AgNO_3$), silver acetate, silver carbonate, silver fulminate, silver oxide, silver perchlorate, silver phosphate, silver thiocyanate, and mixtures thereof. Preferably, silver nitrate ($AgNO_3$) is used in view of wound healing effects.

The silver-containing compound may be added in an amount of 0.01-10% 10% w/v, preferably 0.1-6% w/v. If the amount of silver-containing compound added is less than 0.01% (w/v), the wound dressing cannot substantially exhibit antibacterial activity, and if it is more than 10.0% (w/v), silver alone will remain as particles that can be harmful to the human body.

In the present invention, the coating solution can be prepared by dissolving water-soluble chitosan in water, and then adding the silver compound thereto. Alternatively, the coating solution can also be prepared by preparing, an aqueous solution of chitosan and an aqueous solution of the silver compound, and then mixing these aqueous solutions with each other.

Once the coating solution is prepared by mixing, the hydroxyl (OH−) group of the water-soluble chitosan is ionically bonded with silver ions (Ag+) produced by dissociation of the silver compound, thereby forming chitosan-silver nanoparticles. The coating solution containing chitosan-silver nanoparticles is adsorbed and coated onto a foam dressing to prepare an antibacterial foam dressing.

The coating solution can be coated onto the foam dressing by a coating method such as spray coating, dip coating, flow coating or spin coating, thereby adsorbing the coating onto the foam dressing.

The foam dressing, adsorbed and coated with the coating solution, is dried at a temperature of preferably 200° C. or lower. If the drying temperature is higher than 200° C., the physical properties of the foam dressing will be changed so that the desired effect cannot be obtained.

If required, the preparation method may comprise, after coating but before drying the foam dressing, a step of blowing air into the foam dressing at a pressure of 0.1 $kgf/cm^2$ or higher to ensure pores. The pores of the foam dressing are highly likely to be clogged by adsorption of the coating solution, and to prevent this clogging, air blowing is performed.

In addition, the preparation method may further comprise, after drying the foam dressing, a step of crosslinking the chitosan-silver nanoparticles. When the foam dressing is subjected to crosslinking after coating with the chitosan-silver nanoparticles, the chitosan-silver nanoparticles are crosslinked with one another so that the property of releasing silver in a sustained manner becomes better. The crosslinking process can be performed by, for example, soaking the foam dressing in a 1% (w/v) aqueous solution of $CaCl_2$, glutaraldehyde or tripolyphosphate (TPP) or spraying the aqueous solution onto the foam dressing. After crosslinking, the foam dressing is, in required, blown with air and dried with hot air.

Thus, the chitosan-silver nanoparticles are uniformly dispersed in the foam dressing adsorbed with the antibacterial coating solution, thereby obtaining an antibacterial wound dressing.

The antibacterial wound dressing prepared by this method can absorb and store water in an amount corresponding to at least 10 times the weight thereof. Thus, when the antibacterial wound dressing is attached to a wound, it maintains a moist environment that provides an environment effective for wound healing, and the chitosan-silver nanoparticles are released from the antibacterial wound dressing to provide an antibacterial effect against the wound.

EXAMPLES

Hereinafter, the present invention will be described in further detail with reference to examples, but the scope of the present invention is not limited by these examples.

Preparation of Chitosan Solutions

First, in order to determine a suitable amount of chitosan that exhibits antibacterial activity, chitosan was added to 1 liter of distilled water to concentrations of 0.018, 0.037, 0.075, 0.125, 0.25, 0.5, 1, 6 and 10% (w/v) and sufficiently stirred at room temperature for 1 hour, thereby preparing chitosan solutions.

A commercially available foam dressing (length: 10 cm, width: 10 cm, and thickness: 3 cm) was soaked in each of the chitosan solutions at room temperature so as to be sufficiently absorbed with each of the chitosan solutions, and then dried with hot air at 50 □ for 24 hours, thereby obtaining antibacterial wound dressings containing water-soluble chitosan.

The antibacterial activities of the water-soluble chitosan-containing wound dressings obtained as described above were measured according to the KS J 4206:2008 shaking flask method, and the results of the measurement are shown in Table 1 below. From the results in Table 1, it was found that the wound dressings having a water-soluble chitosan content of 0.075% or higher exhibited antibacterial activity.

TABLE 1

| Wound dressings | Antibacterial activity (%) | Remarks |
| --- | --- | --- |
| Water-soluble chitosan concentration: 0.000% (w/v) | 0% | |
| Water-soluble chitosan concentration: 0.018% (w/v) | 0% | |
| Water-soluble chitosan concentration: 0.037% (w/v) | 0% | |
| Water-soluble chitosan concentration: 0.075% (w/v) | 5% | |
| Water-soluble chitosan concentration: 0.125% (w/v) | 7.5% | |
| Water-soluble chitosan concentration: 0.25% (w/v) | 9.1% | |
| Water-soluble chitosan concentration: 0.5% (w/v) | 10.2% | |
| Water-soluble chitosan concentration: 1% (w/v) | 30.1% | |
| Water-soluble chitosan concentration: 6% (w/v) | 35.2% | |
| Water-soluble chitosan concentration: 10% (w/v) | 40.2% | |

Examples 1 to 8

Silver nitrate was added to a solution of 0.1 g (0.1% w/v) of water-soluble chitosan in 0.1 liter of distilled water to concentrations of 0.01, 0.05, 0.1, 0.2, 0.4, 1, 2 and 6% (w/v), and then sufficiently stirred at room temperature for 1 hour, thereby preparing coating solutions.

A commercially available foam dressing (length: 10 cm, width: 10 cm, and thickness: 3 cm) was soaked in each of the prepared coating solutions at room temperature so as to be sufficiently absorbed with each of the coating solutions, and then dried with hot air at 50° C. for 24 hours, thereby obtaining antibacterial wound dressings.

The antibacterial activities of the wound dressings prepared as described above were measured according to the KS J 4206:2008 shaking flask method, and the results of the measurement are shown in Table 2 below. From the results in Table 2, it can be seen that the concentration of silver nitrate in the coating solution for the wound dressing is preferably 0.01% (w/v) or higher.

TABLE 2

| Wound dressings | | Antibacterial activity (%) | Remarks |
|---|---|---|---|
| Example 1 | Silver nitrate concentration: 0.01% (w/v) | 10.0% | |
| Example 2 | Silver nitrate concentration: 0.05% (w/v) | 51.5% | |
| Example 3 | Silver nitrate concentration: 0.1% (w/v) | 89.2% | |
| Example 4 | Silver nitrate concentration: 0.2% (w/v) | 95.4% | |
| Example 5 | Silver nitrate concentration: 0.4% (w/v) | 99.9% | |
| Example 6 | Silver nitrate concentration: 1% (w/v) | 99.9% | |
| Example 7 | Silver nitrate concentration: 2% (w/v) | 99.9% | |
| Example 8 | Silver nitrate concentration: 6% (w/v) | 99.9% | |

Figure 2:
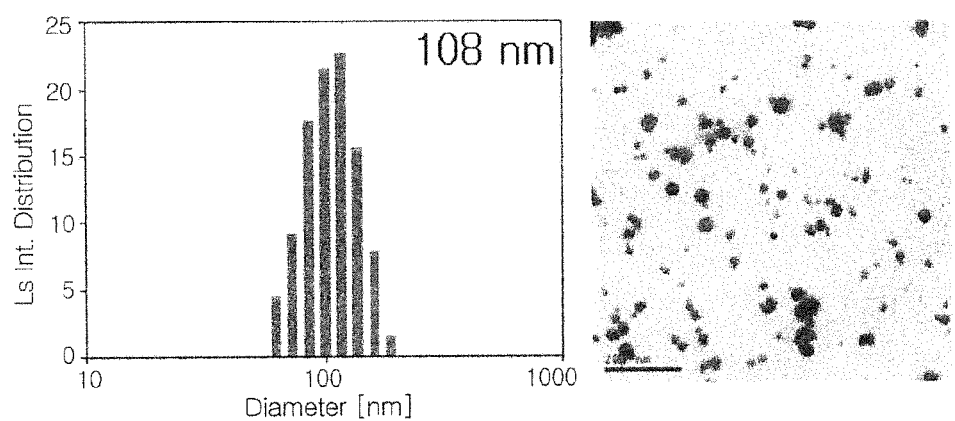
FIG. 2 shows the size and shape of chitosan-silver nanoparticles dispersed in the antibacterial wound dressing of the present invention.

The particle size of chitosan-silver nanoparticles in the coating solution of Example 6 was measured at 632.8 nm using a particle size analyzer with a He-Ne laser at a scattering angle of 90°, and the particles were imaged with a transmission electron microscope. As shown in FIG. 2, the chitosan-silver nanoparticles in the coating solution of the present invention were spherical particles having a narrow particle size distribution and an average particle size of about 100 nm.

Measurement of the Amount of Silver Released

Figure 3:
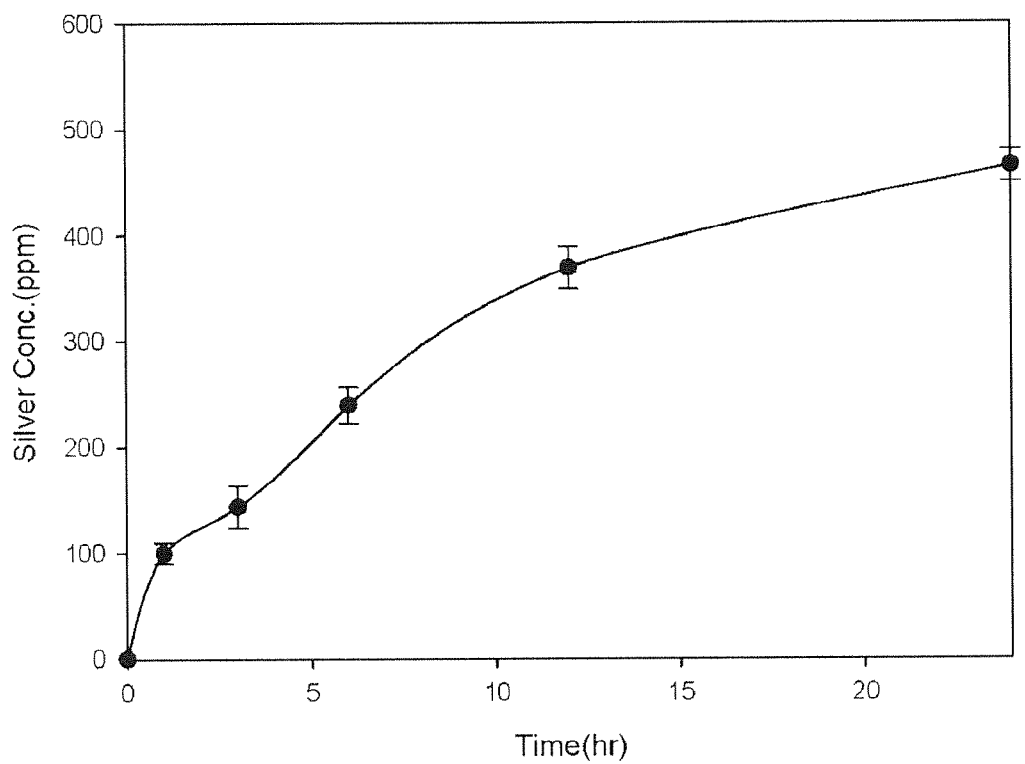
FIG. 3 shows the results of measuring the release of silver from the antibacterial wound dressing of the present invention.

The release of silver from the wound dressing of Example 6 as a function of time was measured. Specifically, each of five wound dressings of Example 6 was placed in 100 mL of a solution of 8.298 g of sodium chloride and 0.368 g of calcium chloride in 20 mL of distilled water, which was similar to exudate. Each of the solutions was taken at 1 hr, 3 hr, 6 hr, 12 hr and 24 hr, and the content of silver in each solution was measured by ICP (inductively coupled plasma atomic emission spectroscopy). The results of the measurement are shown in Table 3 below and FIG. 3. FIG. 3 shows the results of measuring the amount of silver released from the wound dressing of the present invention.

In Table 3, sample 1 indicates the content of silver present in the wound dressing immediately after soaking in the coating solution, and samples 2 to 6 indicate the amounts of silver released when the sample were allowed to stand for varying times.

From the results, it can be seen that 2,060 ppm of silver is present in the initial wound dressing and that, as the standing time increases, the water-soluble polymer is decomposed or the ion bond between chitosan and silver becomes weaker, and thus silver coated on the wound dressing is released slowly.

Meanwhile, for comparison with the present invention, a wound dressing (control) was obtained by coating a foam dressing with only a solution having a silver nitrate concentration of 1%. In the case of the control, it can be seen that the content of silver was only about 10 ppm, and thus silver was not substantially coated and that 10 ppm of silver was completely released after the foam dressing was allowed to stand in air for 1 hour.

From the above-described results, it can be seen that the wound dressing of the present invention has a very excellent sustained-release property, and thus can maintain antibacterial activity for a long period of time.

TABLE 3

| Samples | | Silver content (ppm) | Remarks |
|---|---|---|---|
| Sample 1 | (1% (w/v) silver concentration); total silver content | 2,060 | |
| Sample 2 | (1% (w/v) silver concentration); amount released after 1 hour | 100 | |
| Sample 3 | (1% (w/v) silver concentration); amount released after 3 hours | 124 | |
| Sample 4 | (1% (w/v) silver concentration); amount released after 6 hours | 222 | |
| Sample 5 | (1% (w/v) silver concentration); amount released after 12 hours | 351 | |
| Sample 6 | (1% (w/v) silver concentration); amount released after 24 hours | 460 | |

Measurement of Antibacterial Activity

Figure 4:
FIG. 4 shows the results of testing the antibacterial activity of the antibacterial wound dressing of the present invention against *Staphylococcus aureus* ATCC 6538.
Figure 4:
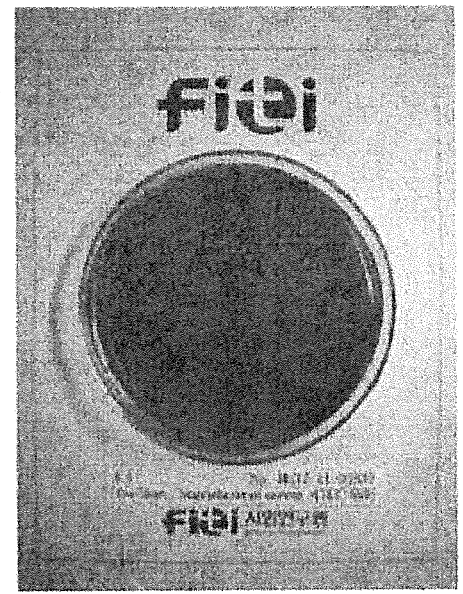
Figure 5:
FIG. 5 shows the results of testing the antibacterial activity of the antibacterial wound dressing of the present invention against *Kleboiella pneumoniac* ATCC 4352.
Figure 5:

The antibacterial activity of the wound dressing of Example 6 was measured according to KS K 0693:2006, and the results of the measurement are shown in Table 4 below and FIGS. 4 and 5 together with the results for the control treated with only a solution having a silver nitrate concentration of 1%. As can be seen in Table 4, the wound dressing of the present invention showed a bacterial reduction rate of 99.9% for *Staphylococcus aureus* ATCC 6538 and *Klebsiella pneumoniase* ATCC 4352, suggesting that the wound dressing of the present invention has a very high antibacterial activity. This fact can also be seen in FIGS. 4 and 5. As shown in FIGS. 4 and 5, in the control not treated with the antibacterial coating solution, large numbers of bacterial cells were cultured, but in the wound dressing treated with the antibacterial coating solution of the present invention, bacterial cells were killed, suggesting that the wound dressing of Example 6 shows high antibacterial activity.

TABLE 4

| | | Control | Example 6 |
|---|---|---|---|
| *Staphylococcus aureus* ATCC 6538 | Initial number of bacterial cells | $2.6 \times 10^4$ | $2.6 \times 10^4$ |
| | After 18 hours | $1.1 \times 10^6$ | <10 |
| | Bacterial reduction rate (%) | — | 99.9% |
| *Klebsiella pneumoniase* ATCC 4352 | Initial number of bacterial cells | $2.4 \times 10^4$ | $2.4 \times 10^4$ |
| | After 18 hours | $2.6 \times 10^7$ | <10 |
| | Bacterial reduction rate (%) | — | 99.9% |

INDUSTRIAL APPLICABILITY

As described above, the antibacterial wound dressing of the present invention slowly releases chitosan-silver nanoparticles, and thus has an excellent sustained-release property so as to be able to maintain antibacterial activity in the wound area of the skin in a moist environment for a long period of time. Thus, it can be widely used fix wound healing.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A method for preparing an antibacterial wound dressing, the method comprising the steps of:
   preparing an antibacterial coating solution using water-soluble chitosan and a silver compound to form chitosan-silver nanoparticles, the coating solution having a chitosan concentration of 0.075-10% w/v and a silver compound concentration of 0.01-10% w/v;
   adsorbing and coating the prepared coating solution onto a foam dressing having a plurality of pores;
   placing the foam dressing adsorbed and coated with the coating solution beneath an air blower; blowing pressurized air of at least 0.1kgf/cm$^2$ onto the top of the foam dressing to prevent clogging of the pores; and
   subsequent to the step of blowing pressurized air, air drying the foam dressing adsorbed and coated with the coating solution at a temperature not to exceed 200° C. to remove excess moisture while maintaining the physical properties of the foam dressing, thereby obtaining a wound dressing uniformly coated with chitosan-silver nanoparticles.

2. The method of claim 1, further comprising, after drying the foam dressing, a step of crosslinking the chitosan-silver nanoparticles.

3. The method of claim 1, wherein the coating solution is coated onto the foam dressing by spray coating, dip coating, flow coating or spin coating.

4. The method of claim 2, wherein the crosslinking is performed by spraying a chitosan crosslinking solution containing CaCl$_2$, glutaraldehyde or tripolyphosphate (TPP) onto the foam dressing.

5. The method of claim 1, wherein the water-soluble chitosan is at least one selected from among water-soluble chitosan lactate, water-soluble chitosan chloride, water-soluble chitosan ascorbate, water-soluble chitosan-PEG and water-soluble chitosan-bile acid.

6. The method of claim 1, wherein the silver compound is one or a mixture of two or more selected from the group consisting of silver bromide, silver iodide, silver fluoride or silver chloride, silver nitrate (AgNO$_3$), silver acetate, silver carbonate, silver fulminate, silver oxide, silver perchlorate, silver phosphate, and silver thiocyanate.

\* \* \* \* \*